United States Patent
Toumazou

(10) Patent No.: US 11,384,403 B2
(45) Date of Patent: Jul. 12, 2022

(54) USE OF POOLED SAMPLES TO OPTIMISE THE EFFICIENCY AND UTILITY OF A RAPID, LAB-FREE POINT-OF-CARE TEST

(71) Applicant: DNANUDGE LIMITED, London (GB)

(72) Inventor: Christofer Toumazou, London (GB)

(73) Assignee: DNANUDGE LIMITED, London (GB)

( * ) Notice: Subject to any disclaimer, the term of this patent is extended or adjusted under 35 U.S.C. 154(b) by 0 days.

(21) Appl. No.: 17/094,190

(22) Filed: Nov. 10, 2020

(65) Prior Publication Data

US 2022/0145405 A1   May 12, 2022

(51) Int. Cl.
  *C12Q 1/68*   (2018.01)
  *C12Q 1/70*   (2006.01)

(52) U.S. Cl.
  CPC .......... *C12Q 1/70* (2013.01); *C12Q 2600/112* (2013.01); *C12Q 2600/156* (2013.01); *C12Q 2600/16* (2013.01)

(58) Field of Classification Search
  None
  See application file for complete search history.

(56) References Cited

U.S. PATENT DOCUMENTS

| | | |
|---|---|---|
| 2018/0087097 A1 | 3/2018 | Toumazou et al. |
| 2020/0347465 A1 | 11/2020 | Schmidt et al. |

FOREIGN PATENT DOCUMENTS

| | | | | |
|---|---|---|---|---|
| WO | WO2007/098184 | * | 8/2007 | ............... C12Q 1/68 |

OTHER PUBLICATIONS

Corman et al.; Euro Surveill. Jan. 23, 2020, vol. 25, pp. 23-30.*
Li et al.; Emerging Microbes and Infections; vol. 9, Jul. 3, 2020; pp. 1489-1496.*
Abdurrahman et al.; Journal of Clinical microbiology, vol. 53, 2015; pp. 2502-2508.*
WHO (How to safely collect sputum samples from patients suspected to be infected with pneumonmic plague; Sep. 2016, pp. 1-8).*
"Molecular diagnostic template for commercial manufacturers", U.S. Food and Drug Administration, 2020.
"Molecular Diagnostic template for laboratories", U.S. Food and Drug Administration, 2020.
Asselah, et al., "COVID-19: Discovery, diagnostics and drug development", J. Hepatology, vol. 74, pp. 168-184, 2020.
DNANUDGE, "CovidNudge Test Instructions for Use", V.4.1, dnanudge.com, Oct. 2020.
Gibani, et al., "Assessing a novel, lab-free, point of care test for SARS-CoV-2 (CovidNudge): a diagnostic accuracy study", The Lancet Microbe, vol. 1, pp. 300-307, 2020.
Martinez, "Clinical samples for SARS-CoV-2 detection: Review of the early literature", Clinical Microbiology, vol. 42 (15), pp. 121-127, 2020.
Tomb, et al., "Retrospective screening for SARS-CoV-2 in Greater Glasgow and Clyde ICUs between Dec. 2019 and Feb. 2020", J. Infection, vol. 81, pp. 476-478, 2020.

* cited by examiner

*Primary Examiner* — Jehanne S Sitton

(74) *Attorney, Agent, or Firm* — Saul Ewing Arnstein & Lehr LLP

(57) ABSTRACT

The present invention relates to the use of pooled samples to optimise the efficiency and utility of a rapid, lab-free point-of-care test. It is applicable in particular, though not necessarily, to tests for SARS-CoV-2.

19 Claims, 6 Drawing Sheets

USE OF POOLED SAMPLES TO OPTIMISE THE EFFICIENCY AND UTILITY OF A RAPID, LAB-FREE POINT-OF-CARE TEST

TECHNICAL FIELD

The present invention relates to the use of pooled samples to optimise the efficiency and utility of a rapid, lab-free point-of-care test. It is applicable in particular, though not necessarily, to tests for SARS-CoV-2.

BACKGROUND OF THE INVENTION

Despite the emergence of new rapid serological tests for COVID-19, molecular testing such as Reverse Transcriptase PCR (RT-PCR) remains the standard of care for detection of SARS-CoV-2 due to its higher sensitivity and specificity [1]. However, standard laboratory RT-PCR can be time consuming and requires samples to be processed in centralised laboratory facilities. Factoring in sample transportation time and the requirement to process samples in batches means that the turnaround time for laboratory RT-PCR testing can often exceed 24 hours. Point-of-care diagnostic tests which can be run outside of traditional laboratory settings have the potential to accelerate clinical decision making and enable effective triage and infection control measures in frontline clinical and community settings.

SUMMARY OF THE INVENTION

The present teaching is based on studies conducted by the applicant into testing more than sample at the same time.

According to a first aspect, there is provided a method a testing a group of individuals for the presence of a disease or condition, the method comprising:

providing a sputum sample from each individual of the group of individuals;

collecting and pooling a portion of each sample, using a device, the device comprising an absorbent material for absorbing at least some of the portion of each sample in order to form a pooled sample absorbed to the absorbent material of the device;

transferring a portion of the pooled sample from the absorbent material of the device to an analyser capable of amplifying, if present in the pooled sample, one or more nucleic acid sequences associated with the disease or condition and analysing the transferred portion of the pooled sample for the presence of said one or more nucleic acid sequences; and wherein a negative result from the analysis indicates that said one or more nucleic acid sequence(s) is not present in the pooled sample and each individual of the group of individuals does not have the disease or condition and a positive result indicates that said one or more nucleic acid sequence(s) is present in the pooled sample and one or more of each individual of the group of individuals may have the disease or condition.

The method described above and the other methods described herein, are particularly suited as point-of-care tests, which may be conducted in hospitals, surgeries, pharmacies, shops, schools, workplaces etc.

Further embodiments of the present teaching are defined by the following numbered clauses and the following description of an exemplary embodiment, which should not be construed as limiting.

1. A method a testing a group of individuals for the presence of a disease or condition, the method comprising:

providing a sputum sample from each individual of the group of individuals;

collecting and pooling a portion of each sample, using a device, the device comprising an absorbent material for absorbing at least some of the portion of each sample in order to form a pooled sample absorbed to the absorbent material of the device;

transferring at least a portion of the pooled sample from the absorbent material of the device to an analyser capable of amplifying, if present in the pooled sample, one or more nucleic acid sequences associated with the disease or condition and analysing the transferred pooled sample or portion of the pooled sample for the presence of said one or more nucleic acid sequences; and wherein a negative result from the analysis indicates that said one or more nucleic acid sequence(s) is not present in the pooled sample and each individual of the group of individuals does not have the disease or condition and a positive result indicates that said one or more nucleic acid sequence(s) is present in the pooled sample and one or more of each individual of the group of individuals may have the disease or condition.

2. The method according to clause 1 and comprising, prior to said step of collecting and retaining a portion of each sample, collecting and retaining a first portion of each sample using a separate device for each sample, each separate device comprising an absorbent material for absorbing the first portion of each said sample, wherein, when a positive result is obtained, subjecting the retained first portion of each sample to analysis, using the or further analyser(s) in order to detect which retained samples contain said one or more sequences associated with the disease or condition and thereby identify which individuals of the group of individuals has the disease or condition.

3. The method according to either of clauses 1 or 2, wherein the disease or condition is a disease or condition, which affects the respiratory tract.

4. The method according to clause 3, wherein the disease or condition, which affects the respiratory tract is an infection, such as a bacterial, viral or fungal infection.

5. The method according to clause 4 wherein the infection is a viral infection and the virus is a common cold, influenza, respiratory syncytial, adeno, or corona virus.

6. The method according to clause 5 wherein the virus is a corona virus including SARS, MERS and COVID-19 (SARS-CoV-2) virus.

7. The method according to clause 6 wherein the corona virus is COVID-19 (SARS-CoV-2).

8. The method according to any preceding clause, wherein the one or more nucleic acids to be detected comprises at least 2, 3, 4, 5, 6, 7, or 8 specific nucleic acid sequences which are specific to the disease or condition.

9. The method according to any preceding clause, wherein the one or more nucleic acids to be detected comprises at most 4, 6, 8, 10, or 12 specific nucleic acid sequences which are specific to the disease or condition.

10. The method according to any preceding clause, wherein the one or more nucleic acids encodes a native or mutant protein associated with the disease or condition.

11. The method according to any of clauses 7-10, wherein the one or more nucleic acids is, or includes the rdrp-IP2, rdrp-IP4, e-gene, n1, n2, and/or n3 gene(s), or specific fragments thereof.

12. The method according to any preceding clause wherein the method includes a positive control, to confirm that the sample or samples contains nucleic acid from the individual or individuals, not associated with the disease or condition and that the sample has been obtained correctly.

13. The method according to clause 12, wherein the nucleic acid, which acts as the positive control is the ribonuclease P gene or specific fragment thereof.

14. The method according to any preceding clause wherein the group of individuals are asymptomatic.

15. The method according to any preceding clause wherein the group of individuals are asymptomatic emergency hospital admissions, staff and/or residents in care homes, family and/or support groups, workplace and/or conference groups, film and/or television production teams, theatre and/or concert production teams, sports teams, and staff and/or students in pre-school, school, college or university.

16. The method according to any preceding clause, wherein the groups comprises at least 2 individuals and up to 40 individuals, such as 2-40, 2-30, 2-20, 2-15, 2-12, 2-10, 2-8, 2-6, or 2-4, as well as any integers and ranges in between.

17. The method according to any preceding clause, wherein the device is in the form of a swab, such as a buccal, nasopharyngeal, or oropharyngeal swab.

18. The method according to clause 17, wherein the swab is a Isohelix™ swab.

19. The method according to any preceding clause, wherein the and/or first portions of the sample are contacted with or inserted a cartridge which is to be introduced, or has been introduced into the analyser.

20. The method according to any preceding clause wherein the analyser is a NudgeBox™ analyser.

21. A method of managing a disease outbreak comprising:
using the method of any preceding clause to determine whether one or more individuals of a group of individuals has said disease or condition;
if such a determination is made, sending the result to the individuals of the group identified as having the disease or condition via an electronic communication means together with an instruction to isolate.

22. A kit for use in a method according to any preceding clause, the kit comprising:
two or more sample receptacles for collecting a respective sputum sample from each of two or more individuals in a group of individuals, each receptacle comprising indicia, or a label specifically designed to identify the sputum sample, with the individual from which is was obtained; and
instructions explaining how to take a sputum sample.

23. A kit for use in a method according to any of clauses 1-21, the kit comprising:
two or more sample receptacles for collecting a respective sputum sample from each of two or more individuals in a group of individuals; and
two or more swabs, each of said two or more swabs comprising an absorbent material for absorbing a first portion of said sample from each of said two or more individuals and two or more respective sealable enclosure devices for receiving said two or more swabs,
wherein each receptacle and/or enclosure device comprises indicia, or a label specifically designed to identify the sputum sample, with the individual from which is was obtained.

24. The kit according to clauses 22 or 23 further comprising
a single pool collection swab comprising an absorbent material for absorbing and pooling a portion of each sample from all individuals in the group of individuals.

25. The kit according to either of clauses 23-24,
further comprising instructions explaining how to take a sputum sample and/or how obtain a pooled sample.

All embodiments described herein should not be construed as limiting and various alternatives will be evident to the skilled addressee. All papers and patents referred to herein and their entire contents are hereby incorporated by way of reference.

DETAILED DESCRIPTION OF THE INVENTION

Figure 1:
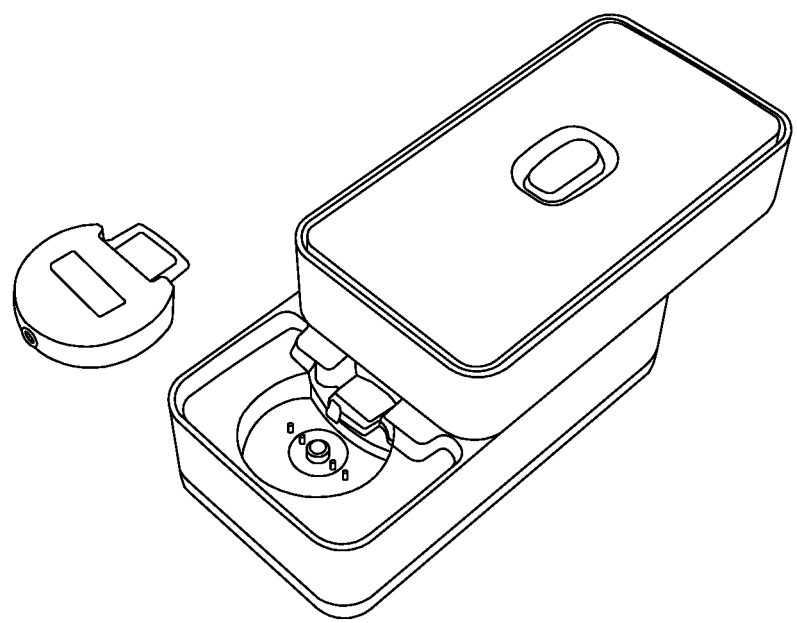
FIG. 1: NudgeBox (28×15-5×13-5 cm; 5 kg) and DnaCartridge (25×78×85 mm; 40 g)

The DnaNudge™ CovidNudge™ test is a point-of-care, real-time RT-PCR test that provides a sample-to-answer diagnosis of SARS-CoV-2 without the need for any laboratory facilities or sample preparation. This is described in detail in more detail and with reference to WO2108055407 and Gilbani and Toumazou [2] to which the skilled reader is directed. The platform comprises a single-use DnaCartridge and a processing unit (the NudgeBox) illustrated in FIG. 1. The DnaCartridge is a disposable, sealed, and integrated lab-on-chip device that enables sample-to-result PCR. The DnaCartridge consists of two main parts: an amplification unit (AU) and a sample preparation unit (SPU). A nasopharyngeal swab sample is inserted directly into the swab chamber of the sample preparation unit immediately after collection. The swab is broken, leaving the swab tip and the sample within the chamber, which is then sealed. Cartridges are placed in the NudgeBox processing unit, which provides the pneumatic, thermal, imaging, and mechanics required to run a real-time RT-PCR reaction outside of a laboratory setting. The sample preparation unit consists of chambers containing buffers to extract and purify RNA from the swab sample, as well as a lyophilised RT-PCR master-mix to mix with the extracted RNA. The DnaCartridge™ fits on top of a motor-driven spigot in the NudgeBox™, which rotates the SPU through each stage of sample processing before filling the wells of the AU, inside which the RT-PCR reaction takes place.

The following description is directed to the detection of SARS-CoV-2, but this should not be construed as limiting and the teaching can easily be extended to the detection of any disease or condition, which can be detected by way of one or more nucleic acid sequences which are associated with the disease or condition to be detected. Examples include respiratory conditions, especially infections caused by bacterial, viral or fungal agents.

The AU comprises dried primers and probes uniquely spotted into 72 reaction wells enabling multiplex analysis. The array comprises six viral targets (rdrp-IP2, rdrp-IP4, e-gene, n1, n2, and n3) and one host gene as a sample adequacy control (Ribonuclease P, RNaseP). Each gene target has nine or ten technical replicates within the array, while the human control has six replicates. Following completion of the PCR reaction, the results from the DnaNudge test are transmitted to the Cloud where an algorithm is run to determine the results [2]. These results are transmitted back to an Operator app run on an iPad, as well as being sent onwards to hospital IT systems, and are reported as positive, negative, indeterminate, invalid or aborted according to Table 1. Following the test, the single-use cartridge is disposed of following standard laboratory disposal procedures.

TABLE 1

DnaNudge test result reporting

| | |
|---|---|
| Invalid | Less than 3 of the 6 human RNASeP replicates have amplified. Viral results are not applicable |
| Positive | At least 3 of the viral gene replicates have amplified. This could be 3 from the same gene type, or 3 from distinct genes. At least 3 human RNASeP replicates have amplified. |
| Negative | None of the viral targets have amplified. At least 3 human RNASeP replicates have amplified. |
| Indeterminate | One or two of the viral targets have amplified. At least 3 human RNASeP replicates have amplified. |
| Error | A technical issue (insufficient pressure) was detected during the test. The test was aborted. |

The diagnostic accuracy of the CovidNudge test was assessed in April and May 2020 by comparing nasopharyngeal swab samples from individuals at three hospitals in London and Oxford against nasal and throat swabs tested on laboratory RT-PCR platforms [2]. The sensitivity of the DnaNudge point-of-care test compared with laboratory-based testing was 94% (95% CI 86-98) with a specificity of 100% (95% CI 99-100). Following this clinical validation, the CovidNudge test achieved the CE Mark in July 2020 enabling the technology to be used as standard of care in UK healthcare settings. Since July, over 20,000 patient samples have been tested on the CovidNudge platform across 8 separate hospital sites in London. Current NHS guidelines state that all patients admitted to UK hospitals must have a test for COVID-19; if a rapid test is not available, then patients presenting as emergency admissions must be isolated in side rooms until their laboratory test is returned, allowing the appropriate care pathway to be determined. These side rooms must then be fully cleaned regardless of the COVID-19 test result before they can be occupied by a subsequent patient, placing additional burden on an already stretched nursing resource.

The deployment of CovidNudge as a point-of-care diagnostic has enabled effective triage and timely therapeutic and infection control interventions for emergency admission patients in clinical areas including adult and paediatric A&E, maternity, mental health and renal transplantation, and the technology has been fully embedded as an integral part of the emergency admission pathway at the deployment sites. With test results available within 90 minutes of sample collection, patients can be admitted into the appropriate care pathway bypassing the need for isolation if test results are negative, while enabling sites to meet operational targets to admit, transfer or discharge patients from A&E within 4 hours.

Sample Pooling

Due to the user-friendly nature of the DnaNudge test with no sample preparation required, in clinical setting the tests are performed by frontline healthcare workers rather than central laboratory staff. The simplicity of use means that each NudgeBox processes one sample at a time, thus each clinical area deploys multiple NudgeBoxes to manage the timely testing of emergency admissions at peak throughput times. Although an increase in testing throughput can be accommodated by deploying additional NudgeBoxes, the use of pooled patient samples has been proposed as a method to increase throughput of molecular testing for SARS-CoV-2 [3, 4]. The US Food and Drug Administration (FDA) currently recommends two approaches to patient specimen pooling [3]. The first method is to pool aliquots of transport media each containing a single patient sample (sample pooling), while the second method is to combine swabs from multiple patients into a single volume of transport media (swab pooling). Both methods have advantages and disadvantages. For sample pooling, the individual patient samples are separately preserved, so that if a pooled test reports a positive result, the patient samples needed for the individual follow-up tests already exist. However, the disadvantage is that, since the volume of each sample is reduced, the analytical sensitivity is decreased (i.e. limit of detection (LOD) increases) because individual samples are further diluted. This limits the practical size of the sample pool; the FDA recommends that the analytical sensitivity of the test with n-sample pooling should be evaluated, starting with a maximum n=5. In contrast, swab pooling does not lead to a reduction in analytical sensitivity since the entire sample from each patient is pooled into a single volume of transport media. However, if the test is reported as positive, there is no way to deconvolve which of the individual samples are positive without taking another sample from each patient in the pool. For this reason, the UK NHS currently only recommends sample pooling for asymptomatic patients [4]. The present teaching may overcome one or more of the above identified disadvantages.

Despite the efficiency gains in testing throughput that can potentially be achieved through pooling, in practice the technique has not been widely used in clinical settings. For standard laboratory-based platforms there may be several contributing factors; many test suppliers have not validated the use of pooling; pooling can potentially delay the reporting of results since if a pooled test reports positive, the individual samples need to be retested; pooling is most efficient when prevalence is low, however low prevalence may reduce testing demand, enabling the volume of tests required to be adequately handled by parallel processing of single patient samples.

For point-of-care testing however, the potential benefits of testing pooled samples may be more easily realised. Near-patient tests such as CovidNudge produce rapid results thus a positive pooled test may be quickly followed up with individual testing, while a negative pooled test allows the elimination from isolation in COVID wards of multiple patients in parallel rather than sequentially. However, neither of the pooling methods described earlier are compatible with the DnaNudge CovidNudge platform. This is because the CovidNudge test eliminates the requirement for swab samples to be diluted in liquid transport media, therefore no simple method exists for combining multiple nasopharyngeal swabs from individual patients. This in part led us to consider the use of alternative fluid samples and sputum, in particular, as an alternative sample media.

Sputum Sampling

To investigate whether sputum samples are compatible with the DnaNudge platform, we undertook a validation study comparing nasopharyngeal swab samples with sputum. Assessment took place using samples from two separate groups: patients admitted to hospital via the emergency department at Chelsea & Westminster NHS Foundation Trust, and members of the London Symphony Orchestra. Testing of emergency admissions at Chelsea & Westminster NHS Foundation Trust was done as a service evaluation approved by the point-of-care committee. Patients over 18 testing positive (n=71) and negative (n=103) on the DnaNudge platform via nasopharyngeal sampling agreed to provide a sputum sample. Members of the London Symphony Orchestra (n=118) were undergoing regular COVID-19 screening on the DnaNudge platform. All participants consented to supplying a sputum sample following the procedure in Appendix 1 in addition to providing a nasopharyngeal swab. Sputum samples were collected into a sample tube (Oragene500, DNAgenotek); the stabilising solution released by the Oragene collection tube has been shown to inactivate the SARS-CoV-2 virus due to the presence of an ionic detergent which renders ineffective enveloped viruses such as SARS-Cov-2 [5].

Figure 2:
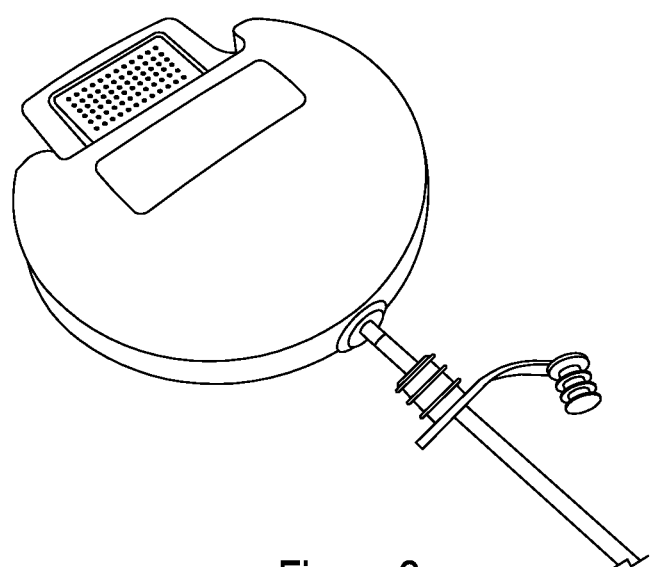
FIG. 2: Cartridge with Isohelix swab (with stopper and bung) inserted into the sample chamber.

Following sputum and nasopharyngeal sample collection, the samples were tested on the DnaNudge platform. To test the sputum samples, an RNA/DNA buccal swab (SK-2, Isohelix) was used. The cap from the swab was removed while retaining the bung with stopper, and the swab was mixed in the sputum in stabilising solution by rubbing gently for 5 seconds to get a good sputum sample on the swab. When extracting the swab from the sample tube, any excess sputum residue hanging from the swab was removed by wiping the swab gently against the inside edge of the tube. The Isohelix swab was then inserted into the cartridge pressing the stopper in place, the swab tail was removed leaving the swab in the chamber, and the cartridge was sealed using the Isohelix bung (FIG. 2). The cartridge was then inserted into the NudgeBox and a test run following standard procedure [2]. 292 paired samples were obtained, and results are shown in Table 2.

TABLE 2

Nasopharyngeal and sputum paired samples tested on the DnaNudge platform. Sputum samples demonstrated 98.6% sensitivity (95% CI = 92.4-99.96%) and 100% specificity (95% CI = 96.9-100%) against nasopharyngeal samples.

|  |  | SPUTUM SAMPLES | |
|  |  | POSITIVE | NEGATIVE |
| --- | --- | --- | --- |
| NASOPHARYNGEAL SAMPLES | POSITVE | 70 | 1 |
|  | NEGATIVE | 0 | 221 |

Figure 3:
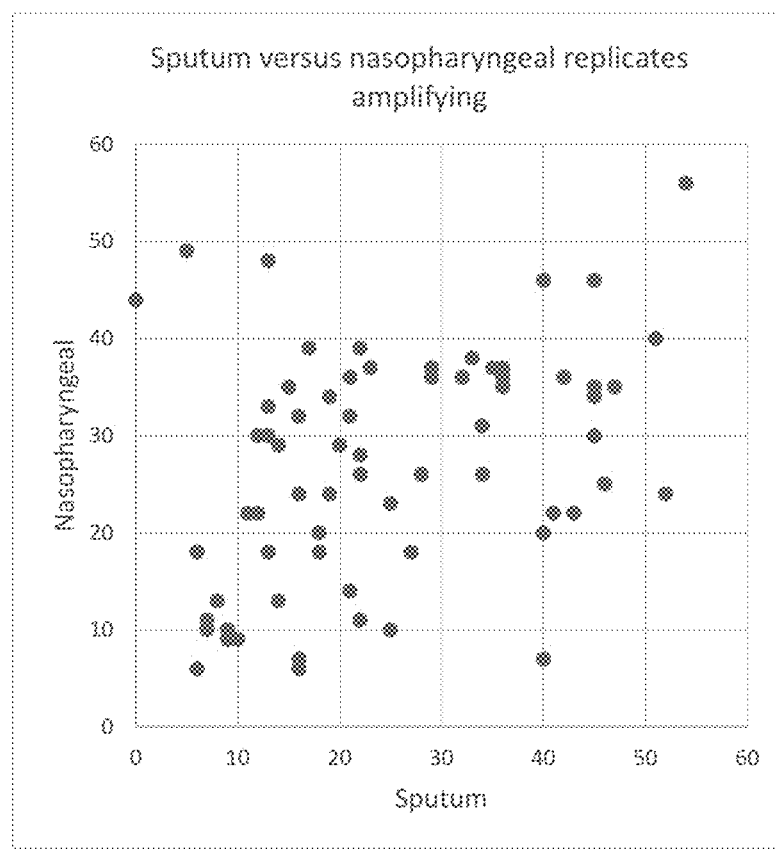
FIG. 3: Number of replicates amplifying on the DnaNudge platform for nasopharyngeal and sputum samples. The data does not suggest that nasopharyngeal or sputum samples present a consistently higher viral load, with significant patient-to-patient variation. The average number of replicates across all samples was similar for both sputum (mean replicates=24.7) and nasopharyngeal (mean replicates=27.1), with the number of replicates amplifying ranging from (5-54) for sputum samples and (6-56) for nasopharyngeal samples.

We quantitively assessed the relative concentration of viral load in nasal and sputum samples by plotting the number of SARS-CoV-2 gene target replicates that amplified in each sample as shown in FIG. 3.

Sputum Pooling

Figure 4:
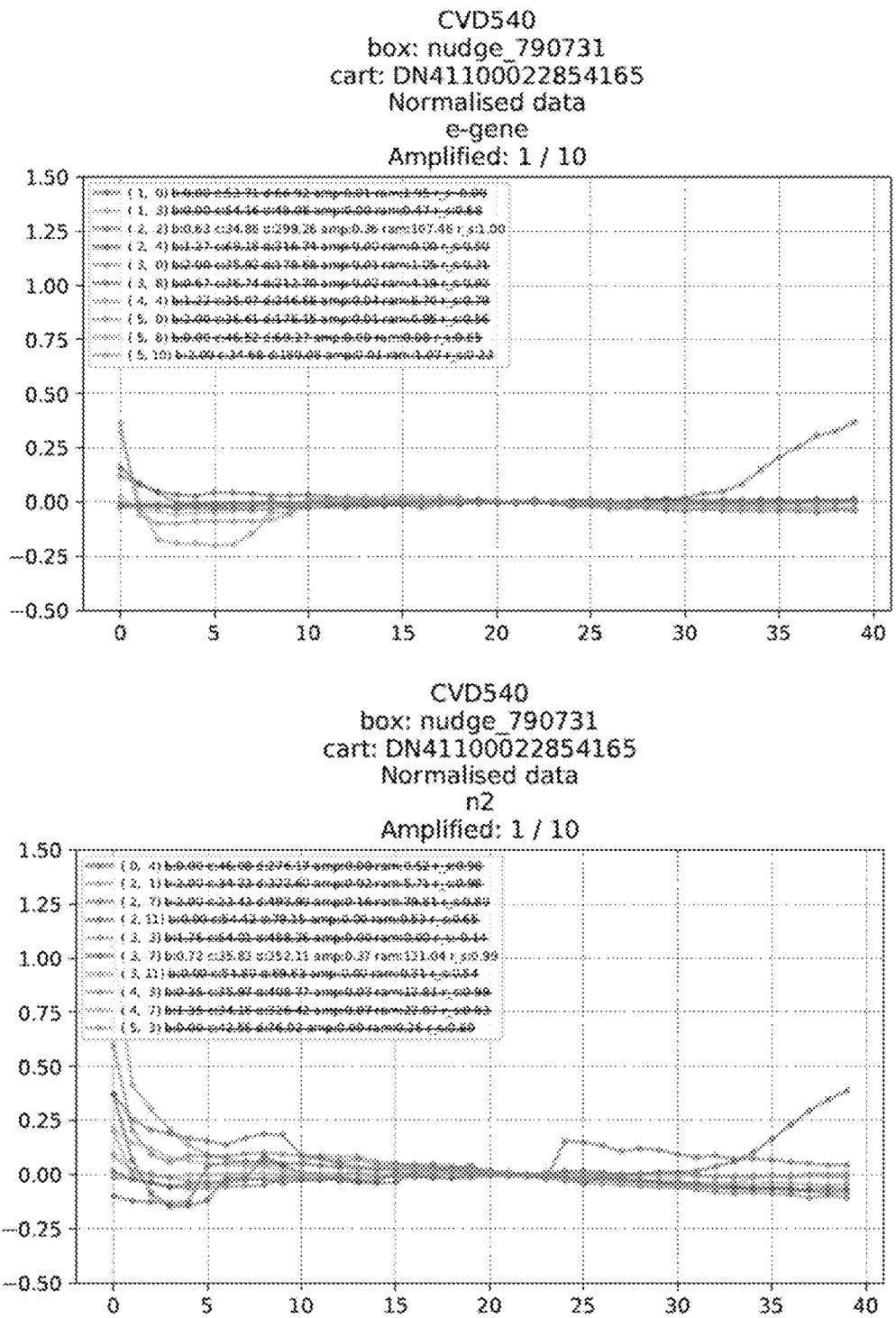
FIG. 4: PCR amplification curves from the DnaNudge platform for a pool of 1 positive and 39 negative samples. For test one (upper figures), one e-gene replicate and one n2-gene replicate amplified. In the second test (lower figure), two n1-gene replicates amplified. Curves with no replicates amplifying are not shown. The positive sample was in position 2 in the pool for both tests.
Figure 4:
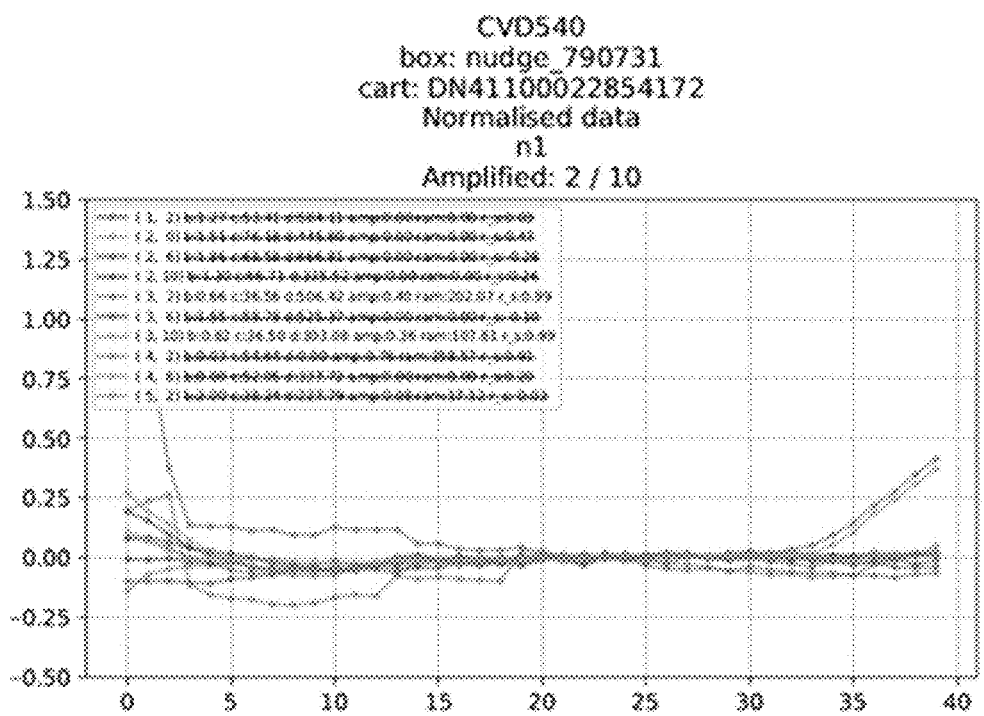

Following the confirmation that sputum is a suitable sample type for the DnaNudge Covid-19 test, we investigated the pooling of multiple sputum samples to increase testing throughput. Pools were tested with one positive sample and the rest as negative samples following the method outlined in Appendix 2. An initial exploratory analysis was performed starting at a pool of two and then incrementing the pool by adding further negative samples. This exploratory analysis was still able to report a positive result from a single positive sputum sample in a pool of 30. A pool of 40 samples was also run twice and both times showed two replicates amplifying, as shown in FIG. 4.

In practice a pool size of 30 or 40 samples is unlikely to be practical unless prevalence is very low, therefore we performed further experiments by choosing a pool size n=10 (NHS guidelines currently recommend a pool size between 6 and 12 [4]). FDA guidelines regarding the validation of n-pooled tests recommend that samples from at least 20 positive patients and (20×n) negative patients should be collected and tested with one positive and (n−1) negative samples per pool [3]. Therefore 20 samples from the positive data set and 180 samples from the negative data set were divided into pools of 10, with one positive and nine negative samples per pool [3]. The samples were selected from the original dataset to cover a range of viral loads (i.e. number of replicates that amplified in the original sample test). The pooled samples were dipped in turn with a single Isohelix swab following the method outlined in Appendix 2, then inserted into a DnaCartridge and tested following standard procedure [2]. The position of the positive sample within the pool was varied to ensure that all possible permutations were tested (i.e. positive sample in first position, second position, . . . ninth position, tenth position), with at least two tests per 'position' of the positive sample. 200 negative samples were also divided into pools of 10 and tested, and results are shown in Table 3.

TABLE 3

Pooled test results. The 200 negative results were tested as 10 pools of 20, while the positive and indeterminate results were tested as one positive sample with nine negative samples. An indeterminate result is when only one or two replicates amplify, i.e. the signal is at the limits of detection.

|  |  | POOLED SAMPLES | | |
|  |  | POSITIVE | INDETER-MINATE | NEGATIVE |
| --- | --- | --- | --- | --- |
| INDIVIDUAL SAMPLES | POSITIVE | 18 | 2 | 0 |
|  | INDETER-MINATE | 0 | 0 | 0 |
|  | NEGATIVE | 0 | 0 | 200 |

Figure 5:
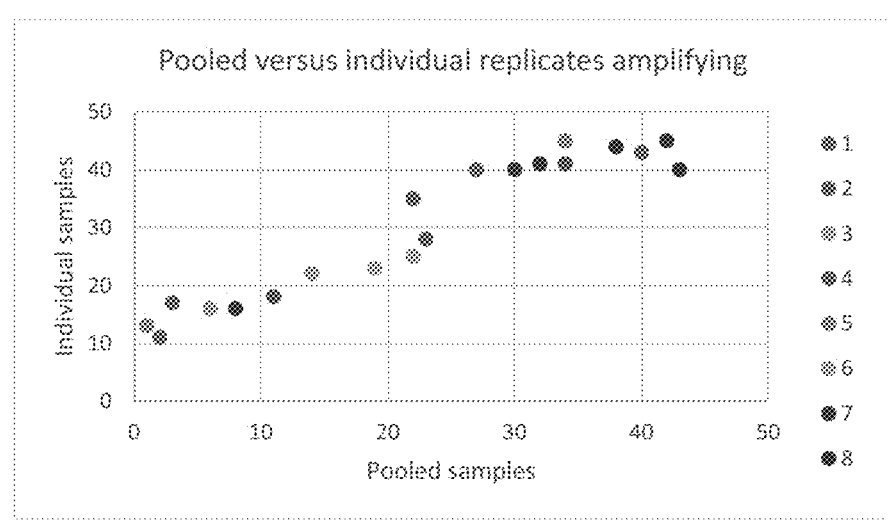
FIG. 5: Number of replicates amplifying for individual and 10-pooled positive samples. Pooled samples in all cases had lower number of replicates amplifying than the original individual samples.

We further examined the number of replicates that amplified (i) when testing the original positive sputum sample, and (ii) when testing the positive sputum sample in a pool of 10, and the results are shown in FIG. 5.

In FIG. 5, the 'position' of the positive sample in the pool is illustrated by the sample colour; no significant correlation between sample position and number of replicates could be seen. This was surprising as it may be expected that the samples would effectively be diluted as more samples are added to the pool and hence reduce the effectiveness of the method. Without being bound by theory, we hypothesize that this may due to the nature of the Isohelix buccal swab which is patterned with a matrix designed to efficiently collect and 'trap' buccal cell samples for DNA testing. This patterned matrix has the effect of securely capturing and holding the sputum samples, and so each additional pooled sample simply adds more sputum material onto the swab matrix.

Limits of Detection for Pooling

Following the qualitative investigation above, a quantitative investigation of the reduction in sensitivity through pooling was performed by assessing the LOD. A negative sputum sample was spiked with viral genetic material (Microbiologics HE0062S process control pellet) dissolved in molecular water. The viral solution was serially diluted and aliquots of 25 uL were added to a 25 uL sputum sample and absorbed onto an Isohelix swab for testing. For individual sample testing the LOD was measured as 250 copies per swab; this rose to 1250 copies per swab for 10 pool testing. The 5-fold increase in LOD for a 10-pool test demonstrates that dipping a swab into successive sputum samples provides less sample dilution than would be expected through traditional sample pooling, where an n-fold reduction in viral concentration would be expected for an n-pool test.

Putting Pooling into Practice

The efficiency gained through pooling of samples is highly dependent on the prevalence of positive patients in the cohort to be tested. If prevalence is very high, pooling can lead to a decrease in testing efficiency due to the need to repeat individual follow-up tests when the pooled sample returns a positive result, and pooling is not recommended when prevalence rises above 10% [4, 5]. We investigated the average efficiency of pooling as a function of prevalence, where the probability P(neg) of returning a negative result from a pooled test is calculated as:

$$P(neg)=(1-(1-p)^n)$$

where p=prevalence and n=pool size. We considered two scenarios:

Single pooled test: in this scenario, if the pooled test is reported as positive, the patient samples are all individually tested to determine which of the samples is positive Nested pooled test: in this scenario if the pooled test is positive, smaller patient pools are repeated to narrow down the search for the positive result(s).

A nested pooled test can be denoted as (n1|n2|n3 . . . . |nx), where n1>n2>n3 . . . >nx, and where n1 denotes the size of the first pool, n2, n3 etc. are the sizes of subsequent sub-pools, and nx=1. So a pooling strategy of (12|3|1) would start with an initial pool size of 12, followed by 4 pooled tests of 3 samples each, followed by individual testing of any of the n=3 sub-pools that had tested positive. Using this nomenclature, the single pooled test can be considered as a nested pool of (n|1), i.e. if the initial n-pool tests positive, the next round of testing would test all n samples individually.

To explore the relative efficiency of single and nested pooling, we simulated the result of different pooling scenarios. We selected a range of single and nested pooling scenarios, with a maximum initial pool size of 12 as per Public Health England (PHE) guidelines [3]. We also limited the total number of nested testing cycles to three (i.e. one or two rounds of pooling with a final individual testing round). This is because three rounds of testing has already tripled the time required to receive a final result for a positive patient; further rounds of pool testing would delay the result further and may detract from the benefit of having a rapid test at the point of care.

Figure 6:
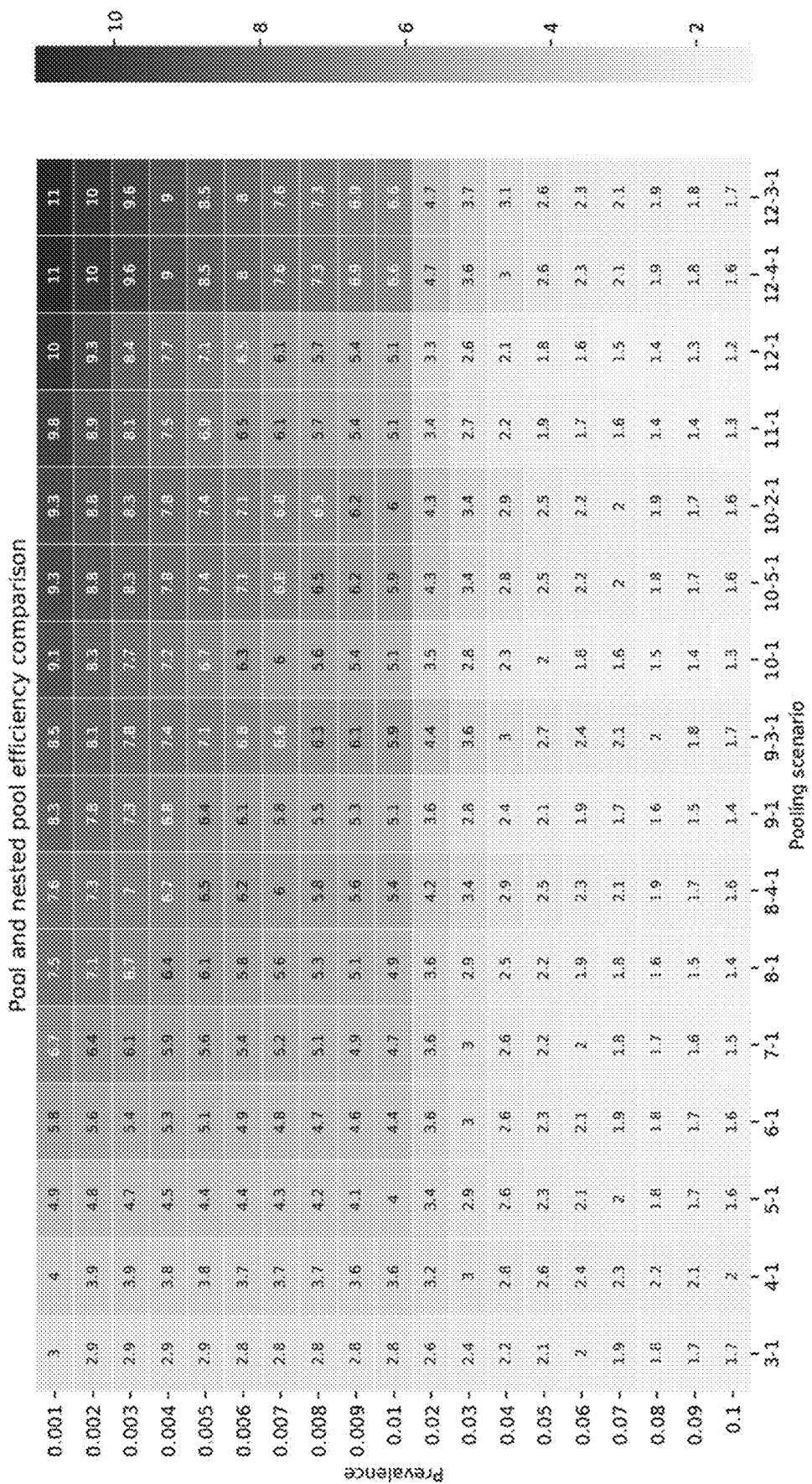
FIG. 6: Relative efficiency (in terms of average number of tests performed) for various pooling strategies, as compared to individual testing only. Pools of up to 12 were analysed as the maximum recommended by UK NHS [4]. For the scenarios simulated, all pooling strategies have an efficiency greater than 1 for prevalence up to 10%. In all cases simulated, the nested pooling scenario results in a higher efficiency than the simple pooling case; however the trade-off is a longer wait for the final confirmatory result in case of a positive result in one or more of the pooled samples.

For each initial pool size, all possible input sample permutations were evaluated. For a pool size of n, this results in 2n input sample vectors. Each input vector was evaluated in turn to determine the total number of tests that would need to be run in the given pooling scenario. Finally, the probability of the specific input vector being realised was calculated as a function of prevalence. This enabled the calculation of the relative efficiency for different pooling strategies as a function of prevalence, and results are summarised in FIG. 6.

Figure 7:
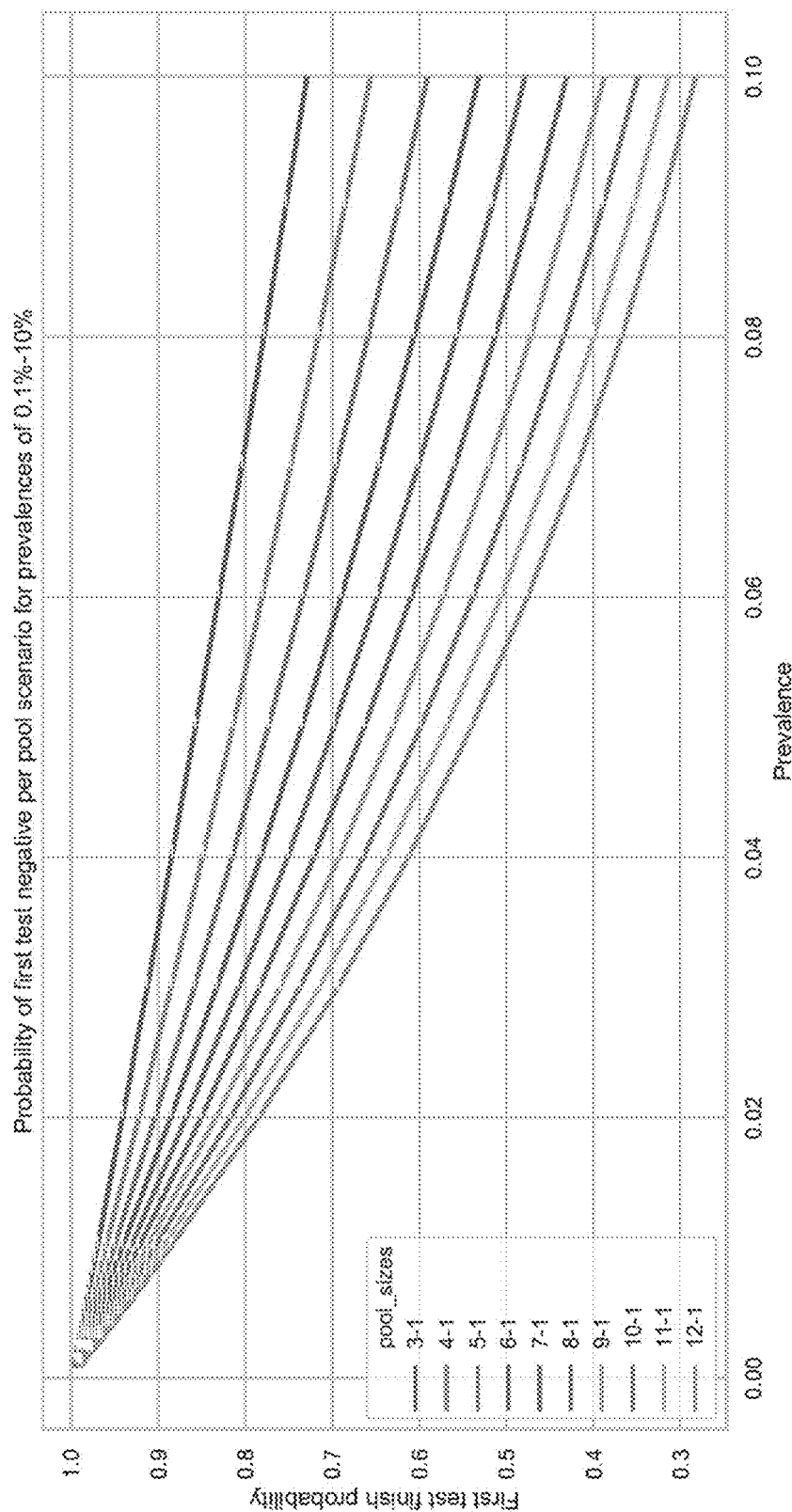
FIG. 7: For prevalence below 2%, pooling of up to 12 samples has a high probability (>75%) of returning a negative result. This would result in a significant increase of testing throughput in an asymptomatic patient cohort. As prevalence increases, to maintain high efficiency of pooling, the pool size should decrease. At 5% prevalence, to maintain a 75% probability of a negative first test, the pool size should decrease to 5.

FIG. 7 shows the probability of the first pooled test returning a negative result, as a function of prevalence.

These results support the proposal that nested pool testing may be used in accordance with the teaching herein as an alternative to single confirmatory tests.

Practical Use Cases

While pooling of samples has the potential to offer significant efficiency gains, in clinical practice at the point of care it may be of imperative importance to know the definitive result for a patient as soon as possible (e.g. when planning for an emergency surgery). In such settings, the requirement for immediacy of results may rule out the use of pooling to eliminate the risk that a second round of testing may be required. However, there are specific use cases where pooling is not only feasible, but also desirable, particularly when testing asymptomatic population groups. Example use cases cover:

Asymptomatic emergency hospital admissions

Care Homes

Family and Support "Bubbles"

Workplace "Bubbles": Film and television production, theatres and concerts, sports teams School classrooms Our sputum sample validation has demonstrated that a single sputum sample can be dipped by a (clean) swab multiple times and stored to enable repeat testing. This provides a method by which sputum pooling can be simply used in practice without the requirement for pipetting small volumes into a pool to avoid sample cross contamination, which is impractical at the point of care. Once collected, each individual sputum sample is dipped with a separate Isohelix swab(s) following the method in Appendix 1, and the cap of each Isohelix swab is then replaced to store the labelled samples for later processing if necessary. Following, a single Isohelix swab is dipped into each of the pooled samples in turn, and the dipped samples are then discarded as contaminated. If a positive result is returned from the pool test, the Isohelix swabs for the individual samples within the pool are available for retesting.

REFERENCES

[1] Lisboa Bastos M. et al, Diagnostic accuracy of serological tests for covid-19: systematic review and meta-analysis. BMJ 2020; 370:m2516|doi: 10.1136/bmj.m2516

[2] Gilbani M., Toumazou C. et al. Assessing a novel, lab-free, point-of-care test for SARS-CoV-2 (Covid- Nudge): a diagnostic accuracy study. Lancet Microbe. https://doi.org/10.1016/S2666-5247(20)30121-X

[3] Molecular Diagnostic Template for Commercial Manufacturers https://www.fda.gov/medical-devices/coronavirus-disease-2019-covid-19-emergency-use-authorizations-medical-devices/vitro-diagnostics-euas

[4] https://www.england.nhs.uk/coronavirus/publication/pooling-of-asymptomatic-sars-cov-2-covid-19-samples-for-pcr-or-other-testing/

[5] https://www.dnagenotek.com/US/pdf/MK-01430.pdf

APPENDIX 1: TAKING A SPUTUM SAMPLE

Equipment Required
SK-2 buccal swab with tube (Isohelix)
Oragene 500 sample collection tune (DNAgenotek)

i. The healthcare professional should prepare the patient for the procedure by asking them to sit upright, rinse their mouth with water and spit out prior to sputum collection.

ii. The patient should be asked to take a few deep breaths to help loosen secretions; please note, if patient is on a nebuliser, give nebuliser first and wait 10 minutes before taking a sample.

iii. The patient should cover their mouth before forcing out a deep cough to release the sputum. Sputum should be collected in the sample tube provided. Ideally the sputum sample should be no less than the size of a small fingernail.

iv. It is important that the healthcare professional checks the quality of the sputum to ensure it is not simply saliva, but rather sputum (mixture of phlegm and mucous). If the patient is unable to provide any sputum, advise to keep hydrated where possible, and encourage deep breathing to try again in an hour.

v. The sample tube should be held upright in one hand and the funnel lid closed with the other hand by pressing firmly until a loud click is heard. The liquid in the lid will be released into the tube to mix with the sputum.

vi. Holding the tube upright, unscrew the funnel from the tube and discard the funnel as clinical waste. Use the small screw cap to close the sample tube tightly. Shake the capped tube for 5 seconds.

vii. Remove the cap from the Isohelix swab while retaining the bung with stopper, and mix the swab in the sputum, rubbing gently for 10 seconds to get a good sputum sample on the swab. When extracting the swab from the sample tube, remove any excess sputum residue hanging from the swab by wiping the swab gently against the inside edge of the tube.

viii. Remove the cap from the DnaCartridge and insert the swab end at a vertical angle into the Cartridge (the DnaCartridge cap can be discarded)

ix. Press the Isohelix cap with stopper into the DnaCartridge and gently remove tail of the swab, this will leave swab tip and sample in the swab chamber.

x. Discard the swab tail in a "sharps" bin.

xi. Lock the DnaCartridge closed with the Isohelix bung and run the test as per standard procedure.

APPENDIX 2: POOLED TESTS USING SPUTUM SAMPLES

Pooling of samples should only be performed by an experienced nurse or healthcare professional who has been adequately trained in the technique.

Equipment required:
SK-2 buccal swab with tube (Isohelix)
Oragene 500 sample collection tubes (DNAgenotek)
Method i. Obtain a number (up to 10) of individual sputum samples following steps (i)-(vi) in Appendix 1. Samples should be labelled as known positive or negative.

ii. Position all sputum sample tubes in a line using a test tube rack or similar receptacle holder and unscrew the lids of each of the tubes.

iii. Remove cap from Isohelix swab retaining the bung with stopper, and gently dip the swab in the first sputum sample for 5 seconds, performing 2 gentle rubs for each side of the swab against the sputum and the inside of the tube. Remove any excess sputum hanging off the swab by rubbing the swab gently against the inside of the tube.

iv. Once this is done for the first sample, insert the same swab into the next and repeat the process for all 10 samples.

v. Load the Isohelix swab into the DnaCartridge following steps (viii)-(xii) in Appendix 1 vi. Any negative samples that have been dipped with the Isohelix swab after the swab has been dipped into a positive sample must be discarded as contaminated.

The invention claimed is:

1. A point-of-care testing method of testing a group of individuals for the presence of a disease or condition, the method comprising:
   providing a sputum sample from each individual of the group of individuals;
   collecting and pooling a portion of each individual's sample, using a device, the device comprising an absorbent material for absorbing at least some of the portion of each sputum sample in turn in order to form a pooled sample absorbed to the absorbent material of the device;
   transferring at least a portion of the pooled sample from the absorbent material of the device to an analyser and using the analyser to analyse the transferred pooled sample or portion of the pooled sample for the presence of one or more nucleic acid sequences associated with the disease or condition; and
   wherein a negative result from the analysis indicates that said one or more nucleic acid sequence(s) is not present in the pooled sample and each individual of the group of individuals does not have the disease or condition and a positive result indicates that said one or more nucleic acid sequence(s) is present in the pooled sample and one or more of each individual of the group of individuals may have the disease or condition.

2. The method according to claim 1 and comprising, prior to said step of collecting and pooling a portion of each individual's sample, collecting and retaining a first portion of each individual's sample using a separate device for each sample, each separate device comprising an absorbent material for absorbing the first portion of each said sample, wherein, when a positive result is obtained, subjecting the retained first portion of each individual's sample to analysis, using the analyser or one or more further analyser(s) in order to detect which retained first portion of each individual's sample contains said one or more sequences associated with the disease or condition and thereby identify which individual or individuals of the group of individuals has the disease or condition.

3. The method according to claim 1, wherein the disease or condition is a disease or condition, which affects the respiratory tract.

4. The method according to claim 3, wherein the disease or condition, which affects the respiratory tract is an infection, selected from the group consisting of a bacterial, viral and fungal infection.

5. The method according to claim 4 wherein the infection is a viral infection and the virus is selected from the group consisting of a common cold, influenza, respiratory syncytial, adeno, and corona virus.

6. The method according to claim 5 wherein the virus is a corona virus selected from the group consisting of SARS, MERS and COVID-19 (SARS-CoV-2) virus.

7. The method according to claim 6 wherein the corona virus is COVID-19 (SARS-CoV-2).

8. The method according to claim 1, wherein the one or more nucleic acids to be detected comprises at least 2, 3, 4, 5, 6, 7, or 8 specific nucleic acid sequences which are specific to the disease or condition.

9. The method according to claim 1, wherein the one or more nucleic acids to be detected comprises at most 4, 6, 8, 10, or 12 specific nucleic acid sequences which are specific to the disease or condition.

10. The method according to claim 1, wherein the one or more nucleic acids encodes a native or mutant protein associated with the disease or condition.

11. The method according to claim 7, wherein the one or more nucleic acids of COVID-19 (SARS-CoV-2) is selected from the group consisting of rdrp-IP2, rdrp-IP4, e-gene, n1, n2, n3 gene(s), or specific fragments thereof and combinations thereof.

12. The method according to claim 1 wherein the method includes a positive control, to confirm that the sample or samples contains nucleic acid from the individual or individuals, not associated with the disease or condition and that the sample has been obtained correctly.

13. The method according to claim 12, wherein the nucleic acid, which acts as the positive control is the ribonuclease P gene or a specific fragment thereof.

14. The method according to claim 1 wherein the group of individuals are asymptomatic.

15. The method according to claim 1 wherein the group of individuals are asymptomatic emergency hospital admissions, staff and/or residents in care homes, family and/or support groups, workplace and/or conference groups, film and/or television production teams, theatre and/or concert production teams, sports teams, and staff and/or students in pre-school, school, college or university.

16. The method according to claim 1, wherein the group comprises at least 2 individuals and up to 20 individuals.

17. The method according to claim 1, wherein the device is in the form of a swab.

18. The method according to claim 2, wherein the first portions of each individual's sample are contacted with or inserted into a cartridge which is to be introduced, or has been introduced into the analyser.

19. A method of managing a disease outbreak comprising:
   using the method of claim 1 to determine whether one or more individuals of a group of individuals has said disease or condition;
   if such a determination is made, sending an electronic communication of the result to the individuals of the group identified as having the disease or condition together with an instruction to isolate.

* * * * *